US00PP29290P2

(12) United States Plant Patent
Westervelt

(10) Patent No.: US PP29,290 P2
(45) Date of Patent: May 15, 2018

(54) *CERCIS* PLANT NAMED 'SJO'

(50) Latin Name: *Cercis canadensis*
Varietal Denomination: Sjo

(71) Applicant: Keith D. Westervelt, Manhattan, KS (US)

(72) Inventor: Keith D. Westervelt, Manhattan, KS (US)

(73) Assignee: BLUEVILLE NURSERY, INC, Manhattan, KS (US)

( * ) Notice: Subject to any disclaimer, the term of this patent is extended or adjusted under 35 U.S.C. 154(b) by 15 days.

(21) Appl. No.: 14/999,746

(22) Filed: Jun. 22, 2016

(51) Int. Cl.
*A01H 5/00* (2018.01)

(52) U.S. Cl.
USPC ..... Plt./216

(58) Field of Classification Search
USPC ..... Plt./216
See application file for complete search history.

(56) References Cited

PUBLICATIONS http://web.extension.illinois.edu/cfiv/homeowners/060420.html
Retrieved from website Aug. 30, 2017 (2 pages total).*

* cited by examiner

*Primary Examiner* — Susan McCormick Ewoldt
(74) *Attorney, Agent, or Firm* — Penny J. Aguirre

(57) ABSTRACT

A new cultivar of *Cercis canadensis* plant named 'Sjo' that is characterized by its flower buds that are dark pink in color and open to flowers that are a blend of light pink and white in color, its upright, slightly arching plant habit, its flowers with sepals that are light to medium reddish pink in color, and its medium-large cordate to deltoid shaped leaves that are medium green in color.

2 Drawing Sheets

Botanical classification: *Cercis canadensis.*
Variety denomination: 'Sjo'.

BACKGROUND OF THE INVENTION

The present invention relates to a new and distinct cultivar of *Cercis canadensis*, and will be referred to hereafter by its cultivar name, 'Sjo'. 'Sjo' is an Eastern redbud tree grown for use as a landscape plant.

The new *Cercis* was discovered by the Inventor in March of 2001 in rural Riley County, Kans. as a naturally occurring branch mutation of an unnamed and unpatented plant of *Cercis canadensis* that was growing in a field production plot.

Asexual propagation of the new cultivar was first accomplished by chip budding onto *Cercis canadensis* rootstock by the Inventor in July of 2001 in rural Riley County, Kans. Asexual propagation by chip budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '' as a unique cultivar of *Cercis canadensis.*

1. 'Sjo' exhibits flower buds that are dark pink in color and open to flowers that are a blend of light pink and white in color.
2. 'Sjo' exhibits an upright, slightly arching plant habit.
3. 'Sjo' exhibits flowers with sepals that are light to medium reddish pink in color.

4. 'Sjo' exhibits medium-large cordate to deltoid shaped leaves that are medium green in color.

The parent plant of 'Sjo' differs from 'Sjo' in having flowers that are lavender in color. 'Sjo' can also be compared to the *Cercis canadensis* cultivars 'Texas White' (not patented), and 'Vanilla Twist' (U.S. Plant Pat. No. 22,744). 'Texas White' differs from 'Sjo' in having flowers that are pure white in color, in having leaves that are darker green in color, and in having a smaller overall plant habit. 'Vanilla Twist' differs from 'Sjo' in having a weeping plant habit, in having leaves that are light green in color, in having leaves that are larger in size, and in having flowers that are pure white in color.

BRIEF DESCRIPTION OF THE DRAWINGS

The accompanying colored photographs illustrate the overall appearance and distinct characteristics of the new *Cercis*. The photographs were taken of a 15 year-old plant as grown outdoors in a trial plot in rural Riley County, Kans.

The photograph in FIG. 1 provides a view of the plant habit and foliage of 'Sjo'.

Figure 1:
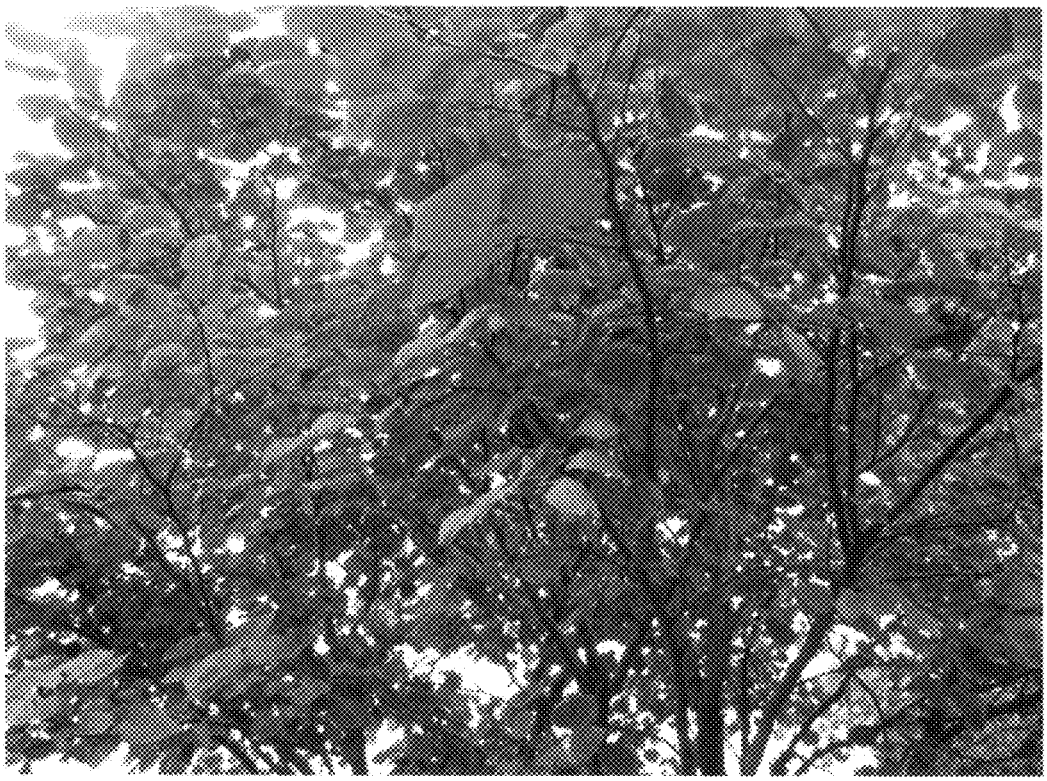
Figure 2:
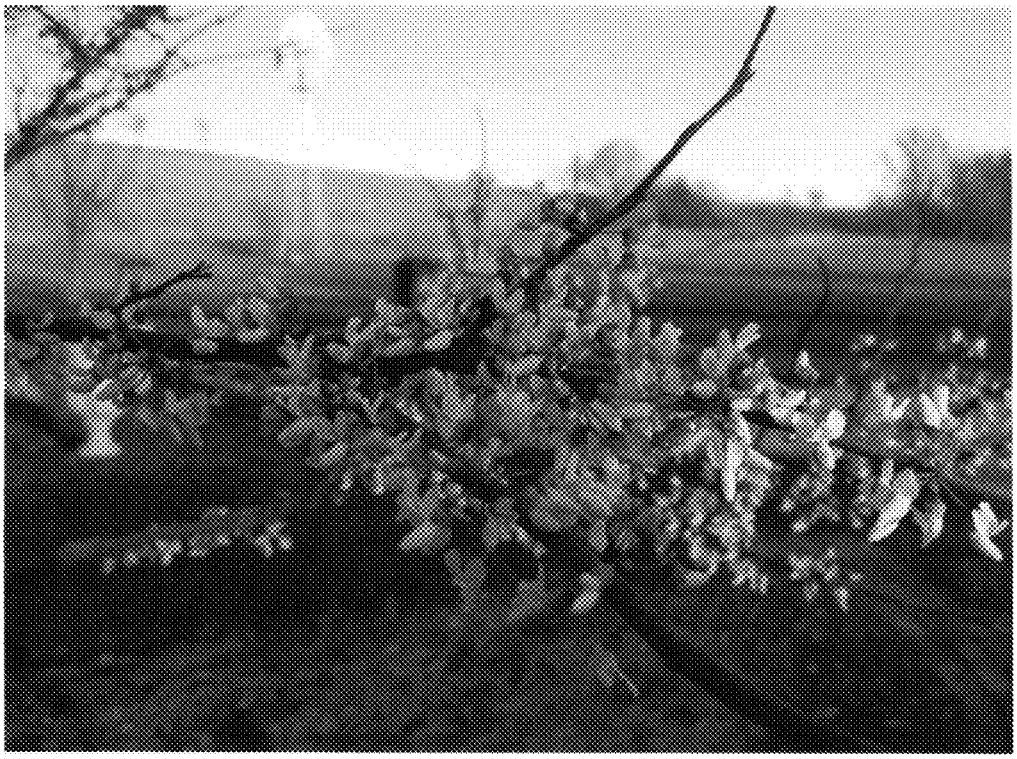

The photograph in FIG. 2 provides a close-up view of the inflorescences of 'Sjo'.

The colors in the photographs are as close as possible with the digital photography techniques available, the color values cited in the detailed botanical description accurately describe the colors of the new *Cercis*.

DETAILED BOTANICAL DESCRIPTION

The following is a detailed description of a 2 year-old plants of the new cultivar as grown outdoors and finished in a 10-gallon container in Park Hill, Okla. with the inflorescence description obtained from a 5 year-old plant grown outdoors in a 15-gallon container in Park Hill, Okla. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Three weeks in March in Park Hill, Okla.

*Plant type*.—Deciduous tree.

*Plant habit*.—Upright and moderately branched.

*Height and spread*.—Reaches about 7.6 m in height and 4.6 m in spread as a ten year-old tree in the landscape.

*Cold hardiness*.—At least to U.S.D.A. Zone 5.

*Diseases and pests*.—No susceptibility or resistance to diseases or pests has been observed.

*Root description*.—Fibrous, 165A to 165B in color.

*Propagation*.—Chip budding onto *Cercis canendensis* rootstock.

*Propagation timing*.—Budding in August, growth begins in the spring and takes 7 months to become a salable whip or mature in the container.

*Growth rate*.—Moderately vigorous.

Branch description:

*Branch shape*.—Rounded, slightly zig-zag in growth habit.

*Branch color*.—New growth, 143A to 143B, lateral branches; 143A to 143B overlaid with a blend between 152A and 197B and heavily covered with lenticels 199B in color, mature bark; N200C and heavily covered with lenticels 199B in color.

*Branch size*.—Main trunk; an average of 2.5 cm in width and 95 cm in length (until lateral branching), lateral branches; an average of 45 cm in length (including new growth) and 6 mm in width, new growth; an average of 2.5 mm in width.

*Branch surface*.—New growth; smooth and satiny, lateral branches and mature bark; glabrous, relatively smooth, and heavily lenticellate.

*Internode length*.—An average of 4 cm.

*Branching habit*.—An average of 12 lateral branches.

Foliage description:

*Leaf shape*.—Cordate to deltoid.

*Leaf division*.—Simple.

*Leaf base*.—Cordate to truncate.

*Leaf apex*.—Acuminate to acute.

*Leaf fragrance*.—None.

*Leaf venation*.—Palmate, color; young and mature leaves upper and lower surface 144B.

*Leaf margins*.—Entire.

*Leaf arrangement*.—Alternate.

*Leaf aspect*.—Held reflexed downward from petiole (hanging).

*Leaf attachment*.—Petiolate.

*Leave number*.—An average of 12 leaves per new growth 30 cm in length.

*Leaf surface*.—New and mature leaf upper surface; smooth, glabrous, satiny and shiny, new and mature leaf lower surface; smooth, glabrous, satiny and dull.

*Leaf size*.—An average of 10 cm in length and 12 cm in width.

*Leaf color*.—New leaf upper and lower surface; 146A, mature leaf upper surface NN137A and lower surface 138B.

*Petiole*.—An average of 3 cm in length and 2 mm in width, held horizontal to about a 15° angle upwards from branch, color 144A, glabrous and satiny surface, flexible and moderately strong.

Inflorescence description:

*Inflorescence type*.—Cauliflorous clusters of papilionaceous (pea-like) flowers.

*Inflorescence size*.—Up to 2.3 cm in width and depth.

*Lastingness of inflorescence*.—2 to 3 weeks.

*Flower size*.—An average of 11 mm in length and 9 mm in width.

*Flower fragrance*.—Faint.

*Flower number*.—An average of 11 flowers per cluster and about 9000 flowers per plant.

*Bracts*.—About 5 per inflorescence, imbricate, ovate in shape, an average of 2.5 mm in length and 2 mm in width, color; 146B with margins 148D, glabrous surface.

*Peduncles*.—An average of 1 cm in length and less than 0.5 mm in width, 64B to 64D in color, glabrous surface, strong, held at all directions from branch node.

*Pedicels*.—None, peduncles attached in cluster at branch.

*Flower buds*.—Lanceolate to cone-shaped, about 5 mm in length and 2 mm in width, color; 62A at the apex fading to 64B to 64D at the base, calyx portion same as open flowers, glabrous surface.

*Flower type*.—Papilionaceous.

*Calyx features*.—Campanulate in shape, comprised of 5 fused sepals; an average of 4.5 mm in length, free apex is an average of 1 mm in length and acute, entire margin color 62C to 62D at the apex transitioning to 64C to MD at the base, glabrous surface.

*Corolla features*.—Papilionaceous, bilateral with two outer petals, a center petal, and an inner labium folded around the stamens and pistil, outer and central petals; obovate to rotund in shape, about 5 mm in length and 3 mm in width, rounded apex, cuneate base, entire margin, color; a blend between 65D and N155C, lightly mottled with 67B towards the center, inner labium; ovate in shape, about 3 mm in length and 3.5 mm in width, rounded apex, cuneate base, entire margins are cupped inward, color; a blend between 65D and N155C, lightly mottled with 67B towards the center, all segments; smooth and glabrous in texture.

Reproductive organs:

*Gynoecium*.—1 Pistil, stigma; ovate in shape, an average of 0.5 mm in length and width, style; an average of 9 mm in length and 0.75 mm in width, color; 64B at the base and 155B at the apex, ovary; superior and inserted obliquely at bottom of calyx and 145D in color.

*Androcoecium*.—About 10 stamens, anther; ovate in shape, an average of 0.75 mm in length and 0.5 mm in width, 163B in color, filament; an average of 9 mm in length and 0.75 mm in width, 155B in color, pollen is moderate in quantity and 14A in color.

*Seed*.—Leguminous seedpod, elliptic-oblong in shape, an average of 6.5 cm in length and 1.2 cm in width, color observed in early summer; 144B with margins and reticulate veins 143A, smooth, satiny upper and lower surface, developed seeds were not observed to date.

It is claimed:

1. A new and distinct cultivar of *Cercis canadensis* plant named 'Sjo' as herein illustrated and described.

* * * * *